(12) United States Patent
Yoo et al.

(10) Patent No.: US 7,803,539 B2
(45) Date of Patent: Sep. 28, 2010

(54) METHOD OF ISOLATING AND PURIFYING NUCLEIC ACIDS USING IMMOBILIZED HYDROGEL OR PEG-HYDROGEL COPOLYMER

(75) Inventors: Chang-eun Yoo, Seoul (KR); Joon-ho Kim, Gyeonggi-do (KR); Kyu-youn Hwang, Incheon-si (KR); Hun-joo Lee, Seoul (KR); Hee-kyun Lim, Gyeonggi-do (KR); Jun-hong Min, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 176 days.

(21) Appl. No.: 11/297,783

(22) Filed: Dec. 7, 2005

(65) Prior Publication Data
US 2006/0134675 A1 Jun. 22, 2006

(30) Foreign Application Priority Data
Dec. 21, 2004 (KR) .................. 10-2004-0109272

(51) Int. Cl.
C12Q 1/68 (2006.01)
C12M 1/34 (2006.01)
C07H 21/00 (2006.01)

(52) U.S. Cl. .................. 435/6; 435/287.2; 536/22.1; 536/25.4

(58) Field of Classification Search .................. 435/6, 435/287.2
See application file for complete search history.

(56) References Cited

U.S. PATENT DOCUMENTS

| | | | |
|---|---|---|---|
| 5,234,809 A | | 8/1993 | Boom et al. |
| 5,705,628 A | * | 1/1998 | Hawkins ................ 536/25.4 |
| 5,804,684 A | * | 9/1998 | Su ........................ 536/25.4 |
| 6,017,577 A | * | 1/2000 | Hostettler et al. ........ 427/2.12 |

(Continued)

FOREIGN PATENT DOCUMENTS

WO WO 00/45792 8/2000

OTHER PUBLICATIONS

Uzawa et al, Synthesis of polyanionic glycopolymers for the facile assembly of glycosyl arrays, 2005, Tetrahedron, 61, 5895-5905.*

(Continued)

*Primary Examiner*—Stephen Kapushoc
*Assistant Examiner*—Narayan K Bhat
(74) *Attorney, Agent, or Firm*—Cantor Colburn LLP

(57) ABSTRACT

Provided is a method of isolating and purifying nucleic acids using an immobilized hydrogel or polyethylene glycol (PEG)-hydrogel copolymer. The method includes: immobilizing a functional group-containing hydrogel or PEG-hydrogel copolymer on a substrate; adding a mixed sample solution containing a salt and nucleic acids to the hydrogel- or PEG-hydrogel copolymer-immobilized substrate to bind the nucleic acids to the hydrogel or the PEG-hydrogel copolymer; washing the nucleic acid-bound hydrogel or PEG-hydrogel copolymer; and eluting the nucleic acids from the hydrogel or the PEG-hydrogel copolymer using an elution solvent. Therefore, binding and elution of nucleic acids can be performed even with no addition of a separate chemical substance, and an effect on a subsequent process such as PCR can be minimized. Furthermore, the amount and intensity for binding nucleic acids can be adjusted according to PEG concentration, and the presence of a hydrogel compound on a substrate enables patterning.

8 Claims, 9 Drawing Sheets

U.S. PATENT DOCUMENTS

| | | |
|---|---|---|
| 6,291,166 B1 | 9/2001 | Gerdes et al. |
| 6,897,072 B1 * | 5/2005 | Rich et al. .................. 436/173 |
| 2003/0218130 A1 * | 11/2003 | Boschetti et al. ............ 250/288 |
| 2004/0043508 A1 * | 3/2004 | Frutos et al. ................ 436/518 |
| 2006/0110594 A1 * | 5/2006 | Frutos et al. ................ 428/332 |

OTHER PUBLICATIONS

Park et al, Synthesis of Arg-Gly-Asp (RGD) sequence conjugated Thermo-Reversible gel via the PEG spacer arm as an extra cellular matrix for pheochromocytoma cell (PC12) culture, 2004, Biosci. Biotechnolog. Biochem., 68, 2224-2229.*

Yoncheva et al, Pegylated nanoparticles based on poly(methyl vinyl ether-co-maleic anhydride): preparation and evaluation of their bioadhesive properties, 2005, European journal of parmaceutical sciences, 24, 411-419.*

Pompe et al, Maleic anhydride copolymers—A versatile platform for molecular biosurface engineering, 2003, Biomacromolecules, 4, 1072-1079.*

Wikipedia brochure on Polyethylene Glycol, printed Nov. 29, 2009.*

Korean Office Action for Application No. 10-2004-0109272 (with English translation ) All references cited, or an English analog, are listed above.

Deggerdal, Arne and Larsen, Frank, "Rapid Isolation of PCR-Ready DNA from Blood, Bone Marrow and Cultured Cells, Based on Paramagnetic Beads," *BioTechniques* (1997) 22: 554-557.

Rudi K. et al., "Rapid, Universal Method to Isolate PCR-Ready DNA Using Magnetic Beads," *BioTechniques* (1997) 22: 506-511.

* cited by examiner 1 min    3 min    5 min

# METHOD OF ISOLATING AND PURIFYING NUCLEIC ACIDS USING IMMOBILIZED HYDROGEL OR PEG-HYDROGEL COPOLYMER

CROSS-REFERENCE TO RELATED PATENT APPLICATION

This application claims priority from Korean Patent Application No. 10-2004-0109272, filed on Dec. 21, 2004, in the Korean Intellectual Property Office, the disclosure of which is incorporated herein in its entirety by reference.

1. Field of the Invention

The present invention relates to a method of isolating and purifying nucleic acids using an immobilized hydrogel or PEG-hydrogel copolymer.

2. Description of the Related Art

Isolation of DNAs from cells is performed using a material capable of binding with DNAs. A material for DNA isolation is for example silica, a glass fiber, an anion exchange resin, and a magnetic bead [Rudi, K. et al., *Biotechniqures* 22, 506-511 (1997); and Deggerdal, A. et al., *Biotechniqures* 22, 554-557 (1997)]. To eliminate hand-intensive tasks and operator errors, several automated machines for large-scale extraction of DNAs were developed.

Purification of nucleic acids using a solid material is known. For example, U.S. Pat. No. 5,234,809 discloses a process for purifying nucleic acids using a solid material capable of binding with nucleic acids. However, the process requires an extended process duration and is not suitable in a Lab-On-a-Chip (LOC) system. Furthermore, the process requires the use of a chaotropic substance. That is, nucleic acids are not bound to a solid material in the absence of a chaotropic substance.

U.S. Pat. No. 6,291,166 discloses a method for archiving nucleic acids using a solid phase matrix. According to this method, since nucleic acids are irreversibly bound to a solid phase matrix, there is an advantage in that a nucleic acid-solid phase matrix composite can be stored for a delayed analysis or a repeated analysis. However, a positively charged substance such as alumina must be activated using an alkaline substance such as NaOH, and irreversible binding of nucleic acids to the activated alumina renders the separation of the nucleic acids from the alumina difficult.

U.S. Pat. No. 5,705,628 discloses a method of isolating DNAs from a solution containing the DNAs, a salt, and polyethylene glycol (PEG) by reversibly and non-specifically binding DNAs to magnetic microparticles with a surface carboxyl group. This method discloses DNA isolation using magnetic microparticles with a surface carboxyl group, a salt, and PEG, but is silent about DNA isolation using a hydrogel or a PEG-hydrogel copolymer, immobilized on a substrate, having a surface carboxyl group.

Common nucleic acid isolation and purification technologies require a separate use of a high-concentration DNA binding reagent, which may affect a subsequent process, such as PCR, and cannot be easily applied to LOC. Therefore, there is a need to develop a DNA isolation technology in which a surface of a solid, such as a substrate, is immobilized with a substance which allows DNAs to bind with the solid surface, even without using a separate DNA binding reagent, and which does not affect a subsequent process.

SUMMARY OF THE INVENTION

Therefore, while searching for solution to the above problems of conventional technologies, the present inventors found that isolation and purification of nucleic acids using a hydrogel or a PEG-hydrogel copolymer immobilized on a substrate does not require the use of a nucleic acid-binding reagent, does not cause the emission of a chemical substance capable of affecting a subsequent process during elution of nucleic acids from a substrate, and enables easy patterning, and thus completed the present invention.

The present invention provides a method of isolating and purifying nucleic acids using an immobilized hydrogel or PEG-hydrogel coplymer in the absence of a separate chemical substance for binding or elution of the nucleic acids, thus minimizing an effect on a subsequent process such as PCR.

According to an aspect of the present invention, there is provided a method of isolating and purifying nucleic acids using an immobilized hydrogel or PEG-hydrogel copolymer, the method including:

immobilizing a functional group-containing hydrogel or PEG-hydrogel copolymer on a substrate;

adding a mixed sample solution containing a salt and nucleic acids to the hydrogel or PEG-hydrogel-immobilized substrate to bind the nucleic acids to the hydrogel or PEG-hydrogel copolymer;

washing the nucleic acid-bound hydrogel or PEG-hydrogel copolymer; and eluting the nucleic acids from the nucleic acid-bound hydrogel or PEG-hydrogel copolymer using an elution solvent.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
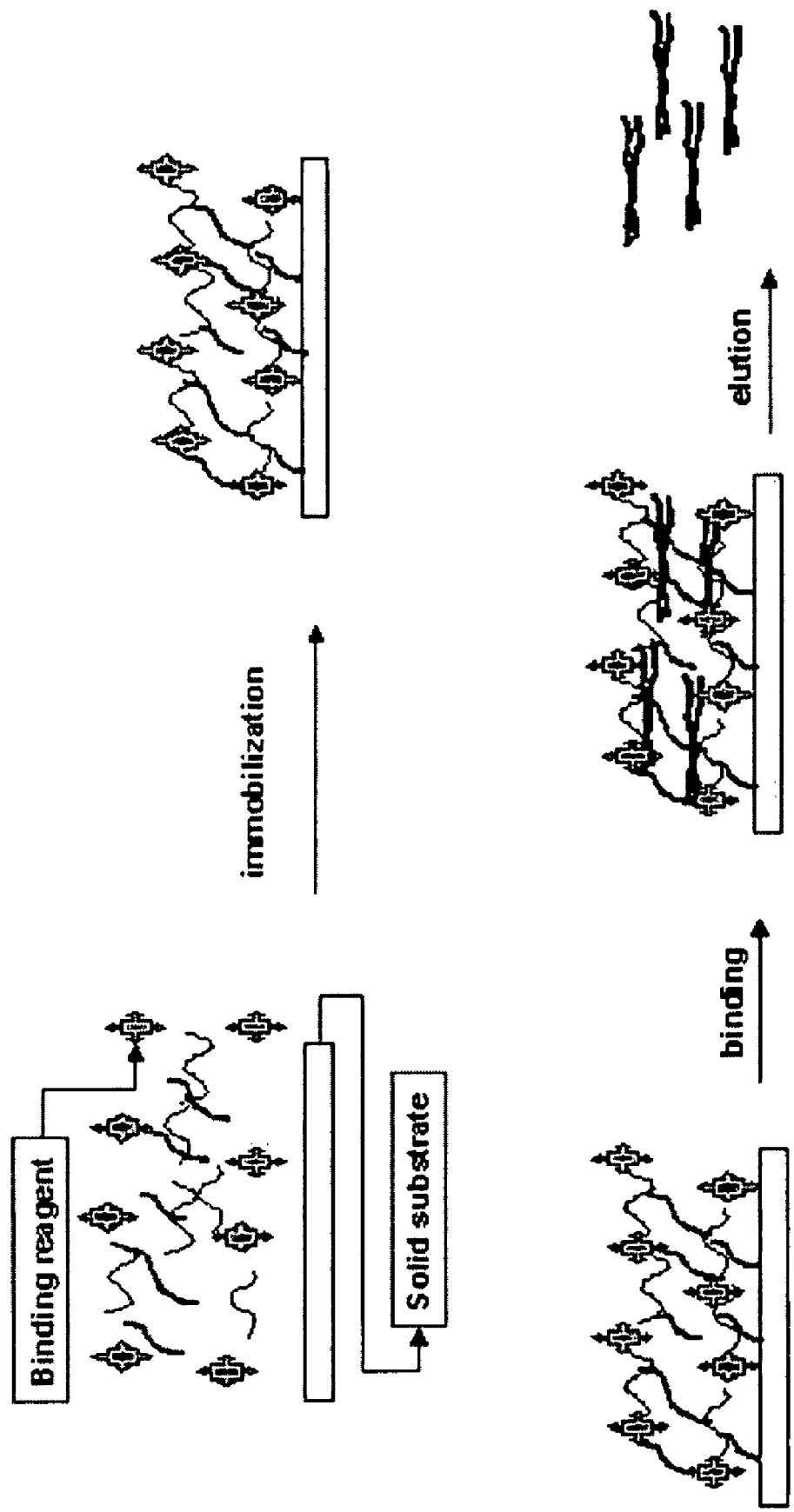
FIG. 1 is a diagram illustrating an example of isolation and purification of nucleic acids according to the present invention.

A method of the present invention includes immobilizing a functional group-containing hydrogel on a substrate. To immobilize a hydrogel on a substrate, hydrogel synthesis on a substrate using a hydrogel precursor is used.

A hydrogel has a large surface area, and is swelled or ionized in response to various stimuli such as pH, electricity, heat, and ions. In this respect, a water-containing hydrogel can be diversely used as food additives, blood contact materials, biodegradable adhesives, contact lenses, injury dressings, artificial organs, drug delivery, DNA vaccines, controlled-release agents, membranes, superabsorbents, cell capsulation and immuno-isolation substances, and carriers for bioactive agents such as drugs. A hydrogel can be classified into an anionic hydrogel and a cationic hydrogel. An anionic hydrogel such as polyacrylic acid is easily swelled and ionized at high pH, low salt concentration, and low temperature. On the other hand, a cationic hydrogel such as poly(N,N-ethylaminoethylmethacrylate) is easily swelled and ionized at low pH and high salt concentration.

A DNA immobilization material must be reversibly bound to DNAs with no addition of a separate chemical substance. Further, a large surface area is required, and processing for application on LOC, for example patterning on a substrate must be possible.

The method of the present invention also includes adding a mixed sample solution containing a salt and nucleic acids on the hydrogel-immobilized substrate to bind the nucleic acids to the hydrogel. When the mixed sample solution containing the salt and the nucleic acids is added to the functional group-containing hydrogel-immobilized substrate, the nucleic acids in the sample solution are bound to the hydrogel. A cationic hydrogel is directly bound to nucleic acids via an electrostatic force, whereas the binding of an anionic hydrogel to nucleic acids is mediated by a salt or PEG/salt.

The method of the present invention also includes washing the nucleic acid-bound hydrogel to eliminate a material unbound to the hydrogel. An organic solvent such as a 70% ethanol may be used as a washing solution. A washing condition may be changed according to the types of the hydrogel and the nucleic acids to be isolated.

The method of the present invention also includes eluting the nucleic acids from the hydrogel using an elution solvent. The nucleic acid-bound hydrogel, after washed with the washing solution, is dried in air to remove the washing solution, and then the nucleic acids are eluted using the elution solvent. The elution solvent may be water, Tris-HCl/pH 8, $Na_2CO_3$/pH 10, or 10× PCR buffer, but is not limited thereto. Water is preferable. A 10× PCR buffer exhibits a higher DNA recovery than water when used as the elution solvent, but there may arise a problem in that PCR does not occur. Thus, water which exhibits a slightly lower DNA recovery than a 10× PCR buffer but is suitable for PCR is preferable to be used as the elution solvent.

According to an embodiment of the present invention, the immobilized hydrogel may form a copolymer with PEG. To immobilize a PEG-hydrogel copolymer on a substrate, PEG-hydrogel copolymer synthesis on the substrate using PEG and a hydrogel precursor is used. According to currently available reports, coexistence of PEG and a salt increases an interaction between DNAs and carboxyl groups of hydrogels, thus leading to the binding of more DNAs to the hydrogels. For example, synthesis of a PEG-hydrogel copolymer may be performed according to Synthesis Example 2 as will be described later.

According to an embodiment of the present invention, the functional group of the hydrogel is a carboxyl group. The carboxyl group is obtained from a carboxyl derivative. The carboxyl derivative may be carboxyl anhydride but is not limited thereto.

Preferably, the hydrogel precursor may be a polymer represented by formula I below, and more preferably poly(ethylene-alt-maleic anhydride):

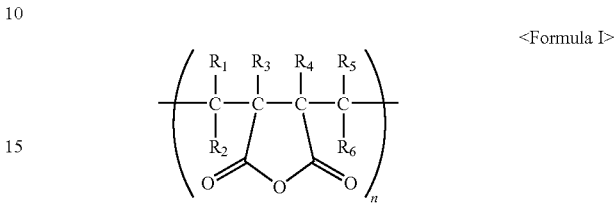

<Formula I> wherein, $R_1$ through $R_6$ are each independently a hydrogen atom, a halogen atom, a hydroxy group, a substituted or unsubstituted alkyl group of 1-20 carbon atoms, a substituted or unsubstituted alkoxy group of 1-20 carbon atoms, a substituted or unsubstituted alkenyl group of 1-20 carbon atoms, a substituted or unsubstituted aryl group of 6-30 carbon atoms, a substituted or unsubstituted aryloxy group of 6-30 carbon atoms, a substituted or unsubstituted heteroaryl group of 2-30 carbon atoms, or a substituted or unsubstituted heteroaryloxy group of 2-30 carbon atoms; and n is an integer from 2 to 100,000.

The alkyl group as used herein refers to a linear or branched radical having 1-20 carbon atoms, preferably a linear or branched radical having 1-12 carbon atoms, and more preferably a lower alkyl having 1-6 carbon atoms. Examples of the alkyl group include methyl, ethyl, n-propyl, isopropyl, n-butyl, isobutyl, sec-butyl, t-butyl, pentyl, iso-amyl, and hexyl. A lower alkyl radical having 1-3 carbon atoms is more preferable.

The alkoxy group as used herein refers to an oxygen-containing linear or branched alkyl radical having 1-20 carbon atoms. A lower alkoxy radical having 1-6 carbon atoms is preferable. Examples of the lower alkoxy radical include methoxy, ethoxy, propoxy, butoxy, and t-butoxy. A lower alkoxy radical having 1-3 carbon atoms is more preferable. The alkoxy radical may be substituted by one or more halo atoms such as fluoro, chloro, or bromo, to give a haloalkoxy radical. A lower haloalkoxy radical having 1-3 carbon atoms is more preferable. Examples of the haloalkoxy radical include fluoromethoxy, chloromethoxy, trifluoromethoxy, trifluoroethoxy, fluoroethoxy, and fluoropropoxy.

The alkenyl group as used herein refers to a linear or branched aliphatic hydrocarbon group containing a carbon-carbon double bond and 2-30 carbon atoms. Preferably, the alkenyl group has 2-12 carbon atoms, and more preferably 2-6 carbon atoms. The "branched alkenyl group" refers to one or more lower alkyl or alkenyl groups appended to a linear alkenyl group. The alkenyl group may be unsubstituted or substituted by one or more non-limiting substituents selected from halo, carboxy, hydroxy, formyl, sulfo, sulfino, carbamoyl, amino, and imino. Examples of the alkenyl group include ethenyl, propenyl, carboxyethenyl, carboxypropenyl, sulfinoethenyl, and sulfonoethenyl.

The aryl group as used herein, which is used alone or in combination, refers to a carbocyclic aromatic system of 6-20 carbon atoms having one or more rings. The rings may be attached to each other as a pendant group or may be fused.

The term "aryl" comprehends an aromatic radical such as phenyl, naphthyl, tetrahydronaphthyl, indane, and biphenyl. Phenyl is more preferable. The aryl group may have 1-3 substituents such as hydroxy, halo, haloalkyl, nitro, cyano, alkoxy, and lower alkylamino.

The aryloxy group as used herein refers to aryl-O—. The definition of the "aryl" in the aryloxy group is as described above.

The heteroaryl group as used herein refers to a monovalent monocyclic or bicyclic aromatic radical of 6-20 carbon atoms containing one, two or three hetero atoms selected from N, O, P and S. The term "heteroaryl" also means a monovalent monocyclic or bicyclic aromatic radical forming N-oxide or a quaternary salt by oxidation or quaternization of a heteroatom in the ring. Examples of such heteroaryl include, but are not limited to, thienyl, benzothienyl, pyridyl, pyrazinyl, pyrimidinyl, pyridazinyl, quinolinyl, quinoxalinyl, imidazolyl, furanyl, benzofuranyl, thiazolyl, isoxazolyl, benzisoxazolyl, benzimidazolyl, triazolyl, pyrazolyl, pyrrolyl, indolyl, 2-pyridonyl, 4-pyridonyl, N-alkyl-2-pyridonyl, pyrazinonyl, pyridazinonyl, pyrimidinonyl, oxazolonyl, and their equivalent N-oxides (e.g., pyridyl N-oxide, quinolinyl N-oxide), and quaternary salts thereof.

The heteroaryloxy group as used herein refers to heteroaryl-O—. The definition of the "heteroaryl" in the heteroaryloxy group is as described above.

Hydrolysis of maleic anhydride which is a repeat unit of the hydrogel precursor produces a polymaleic acid which is a polycarboxyl acid. The polymaleic acid has a similar structure to polyacrylic acid (PAA) which is an anionic hydrogel. Further, the polymaleic acid has a large surface area and can be patterned on a substrate due to its hydrogel characteristics.

According to an embodiment of the present invention, the substrate may be a slide glass, a silicon wafer, a metal plate, a polystyrene film, etc. There are no limitations on the substrate provided that it can be immobilized with a hydrogel polymer. However, the substrate is required to have water insolubility. If the substrate is soluble in water, separation of a nucleic acid-containing solution and the substrate may be difficult. Further, a substrate with a large surface area is preferable since more hydrogel polymers can be bound thereto. To increase a surface area, an even substrate such as a glass or a wafer may be surface-processed into a pillar-shaped substrate.

According to an embodiment of the present invention, the salt is a halogen salt of an alkali metal or an alkali earth metal. The concentration of the salt may be 0.5-5M. Examples of the salt suitable for binding of nucleic acids to a hydrogel include, but are not limited to, halogen salts of alkali metals or alkali earth metals such as sodium chloride, lithium chloride, potassium chloride, calcium chloride, barium chloride, magnesium chloride, and cesium chloride. Sodium chloride is preferable. If the concentration of the salt is less than 0.5M or exceeds 5.0M, the binding efficiency of nucleic acids to a hydrogel may be reduced. More preferably, the concentration of the salt is about 1M.

According to an embodiment of the present invention, the nucleic acids may be oligonucleotides, plasmid DNAs, lambda DNAs, RNAs, PNAs (peptide nucleic acids), LNAs (locked nucleic acids), etc., but are not limited thereto.

According to an embodiment of the present invention, a molecular weight of the PEG may be in the range from 2,000 to 10,000.

According to an embodiment of the present invention, the incorporation ratio of the PEG may be in the range from 1 to 50 mole % based on a carboxyl group. Hydrolysis of one molecule of maleic anhydride group produces 2 molecules of carboxyl group. Here, only one molecule of carboxyl group binds with PEG via an ester bond. Thus, the ratio of PEG is up to 50 mole % based on a carboxyl group.

FIG. 1 is a diagram illustrating an example of isolation and purification of nucleic acids according to the present invention.

Hereinafter, the present invention will be described more specifically with reference to the following examples. The following examples are for illustrative purposes and are not intended to limit the scope of the invention.

EXAMPLES

Synthesis Example 1

Synthesis of PEG-hydrogel Copolymer

Figure 2:
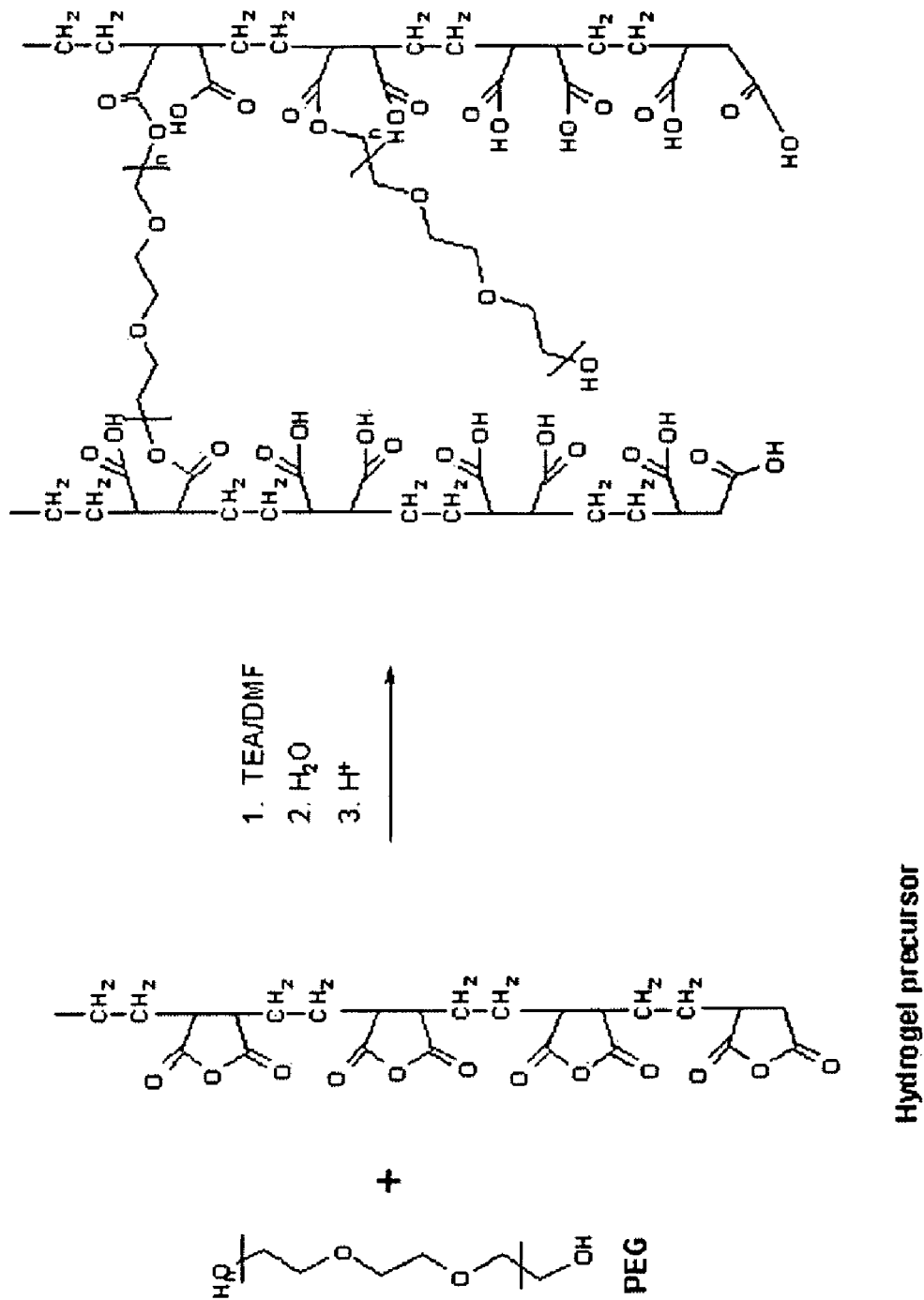
FIG. 2 is a schematic view illustrating the synthesis of a PEG-hydrogel copolymer.

FIG. 2 is a schematic view illustrating the synthesis of a PEG-hydrogel copolymer. In detail, 1.0 g of poly(ethylene-alt-maleic anhydride) (average molecular weight: 300,000) and 0.5 g of PEG (molecular weight: 10,000) were dissolved in 30 ml of N,N-dimethylformamide (DMF). 200 µl of triethylamine (TEA) was added to the reaction mixture with stirring at 40° C. for one hour, cooled to room temperature, 50 ml of water is added thereto and stirred for 30 minutes. The reaction solution was adjusted to pH 3 with 1N HCl, filtered, and dried in vacuum to give a white solid.

Synthesis Example 2

Synthesis of PEG-hydrogel Copolymer on Substrate

Figure 3:
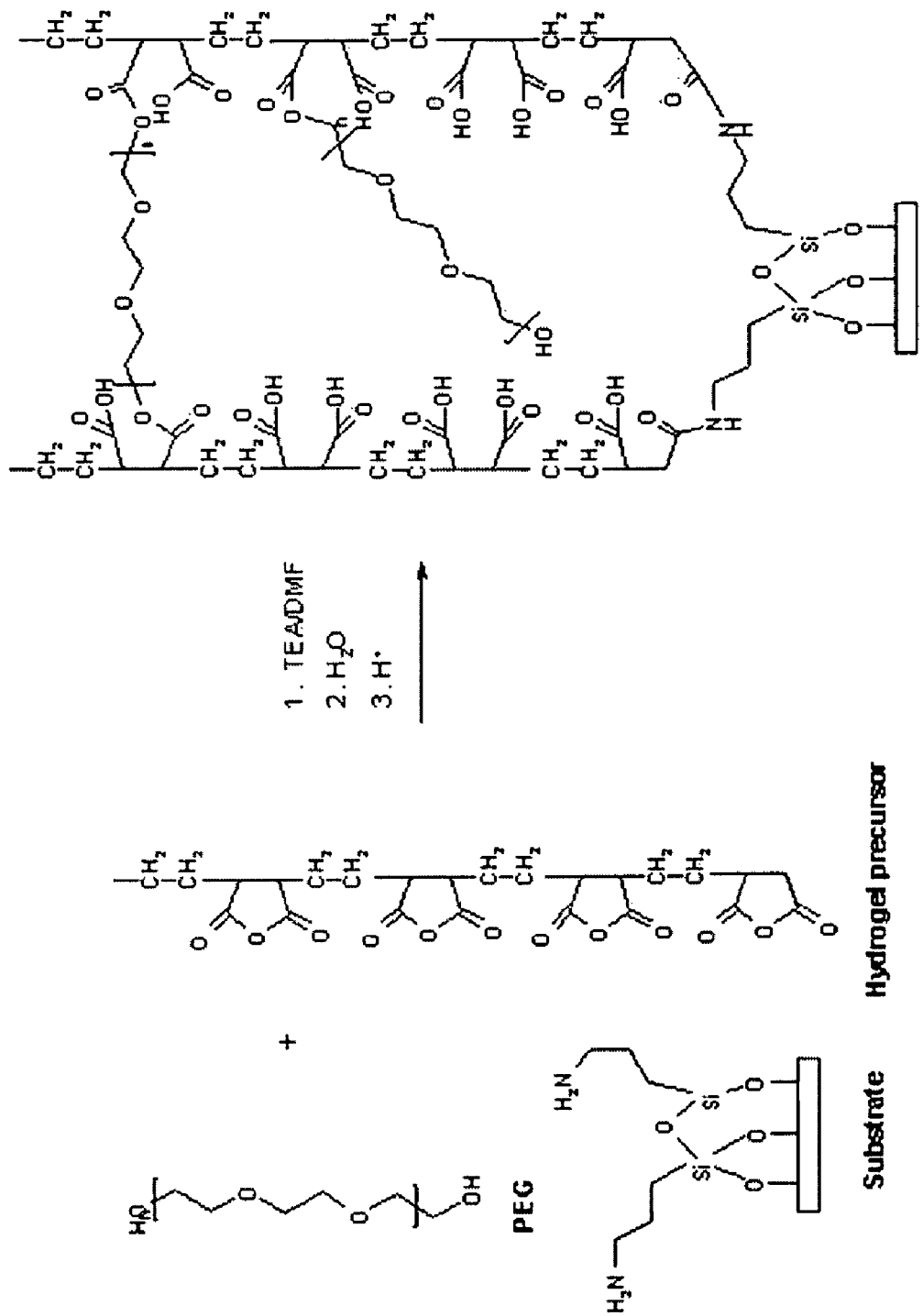
FIG. 3 is a schematic view illustrating the synthesis of a PEG-hydrogel copolymer on a substrate.

FIG. 3 is a schematic view illustrating the synthesis of a PEG-hydrogel copolymer on a substrate. In detail, 0.010 g of poly(ethylene-alt-maleic anhydride) (average molecular weight: 300,000) and 0.158 g of PEG (molecular weight: 10,000, incorporation ratio: 20%) (0.396 g of PEG at incorporation ratio of 50% and 0.634 g of PEG at incorporation ratio of 80%) were dissolved in 10 ml N,N-dimethylformamide. Then, 110 µl of TEA (at PEG incorporation ratio of 20%) (270 µl of TEA at PEG incorporation ratio of 50% and 450 µl of TEA at PEG incorporation ratio of 80%) was added thereto and thoroughly mixed. The reaction mixture was added to a reactor containing a GAPS (γ-aminopropylsilane)-coated substrate and incubated in a 40° C. oven for two hours. After the reaction was terminated, the resultant substrate was washed with 300 ml DMF (×2) and 300 ml acetone (×2), and dried in vacuum. The dried substrate was again placed in the reactor, 10 ml of a 0.1 M Tris buffer (pH 7.5) was added, and the substrate was incubated at room temperature for one hour. After the reaction was terminated, the substrate was washed with 300 ml water (×2) and 300 ml acetone (×2), and dried in vacuum.

Example 1

Swelling Characteristics of PEG-hydrogel Copolymer

Figure 4:
FIG. 4 is a microscopic image showing a swelling behavior of a PEG-hydrogel copolymer with respect to time.

To evaluate the swelling characteristics of a PEG-hydrogel copolymer, 1 ml of a pH 8.0 NaHCO$_3$ (0.025M) solution was added to 0.1 mg of the PEG-hydrogel copolymer synthesized in Synthesis Example 1, and the swelling characteristics of the PEG-hydrogel copolymer with respect to time were observed. FIG. 4 is a microscopic image showing a swelling behavior of the PEG-hydrogel copolymer with respect to time. As shown in FIG. 4, the PEG-hydrogel copolymer was increasingly swelled with time, thus reaching a remarkably increased volume.

Example 2

Synthesis of PEG-hydrogel Copolymers with Different PEG Ratios on Substrate

Figure 5:
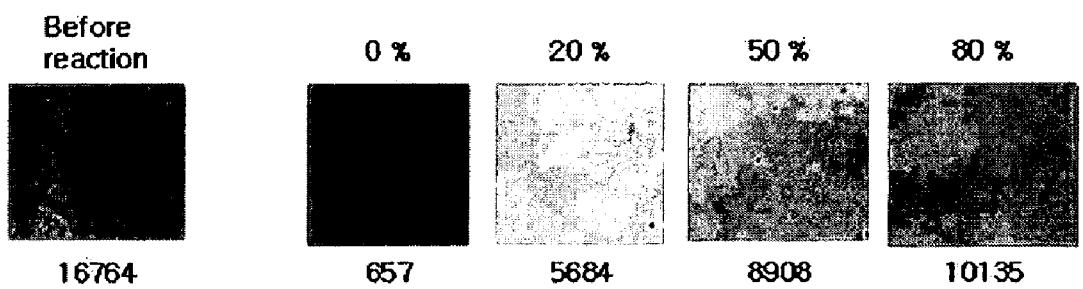
FIG. 5 is a view illustrating relative fluorescence values for reactions of fluorescein isothiocyanate (FITC) and PEG-hydrogel copolymers having different PEG ratios on a GAPS-coated silicon substrate.

To evaluate the degree of synthesis of PEG-hydrogel copolymers on a GAPS-coated silicon substrate according to a PEG incorporation ratio, FITC (fluorescein isothiocyanate) reaction was performed. For this, four PEG-hydrogel copolymers were synthesized in the same manner as in Synthesis Example 2. FIG. 5 illustrates relative fluorescence values for reactions of FITC and the PEG-hydrogel copolymers having different PEG ratios on the GAPS-coated silicon substrate. The FITC emits fluorescence by reaction between it and a free amine group of the substrate. Higher fluorescence intensity indicates the presence of more free amine groups on the substrate, which means a smaller production of a PEG-hydrogel copolymer. As shown in FIG. 5, FITC fluorescence intensity was very high as 16764 before synthesis of a PEG-hydrogel copolymer, whereas it was remarkably reduced after the synthesis of a PEG-hydrogel copolymer. That is, reduction of FITC fluorescence intensity on a silicon substrate after synthesis of a PEG-hydrogel copolymer indicates that a free amine group of the silicon substrate participated in the synthesis of the PEG-hydrogel copolymer. Further, as the incorporation ratio of PEG increased, fluorescence intensity increased. Such an increase in fluorescence intensity is not because a large number of free amine groups react with FITC, but because unreacted hydroxyl groups of PEG react with FITC.

Example 3

Separation of DNAs by PEG-hydrogel Copolymer on Substrate

Figure 6:
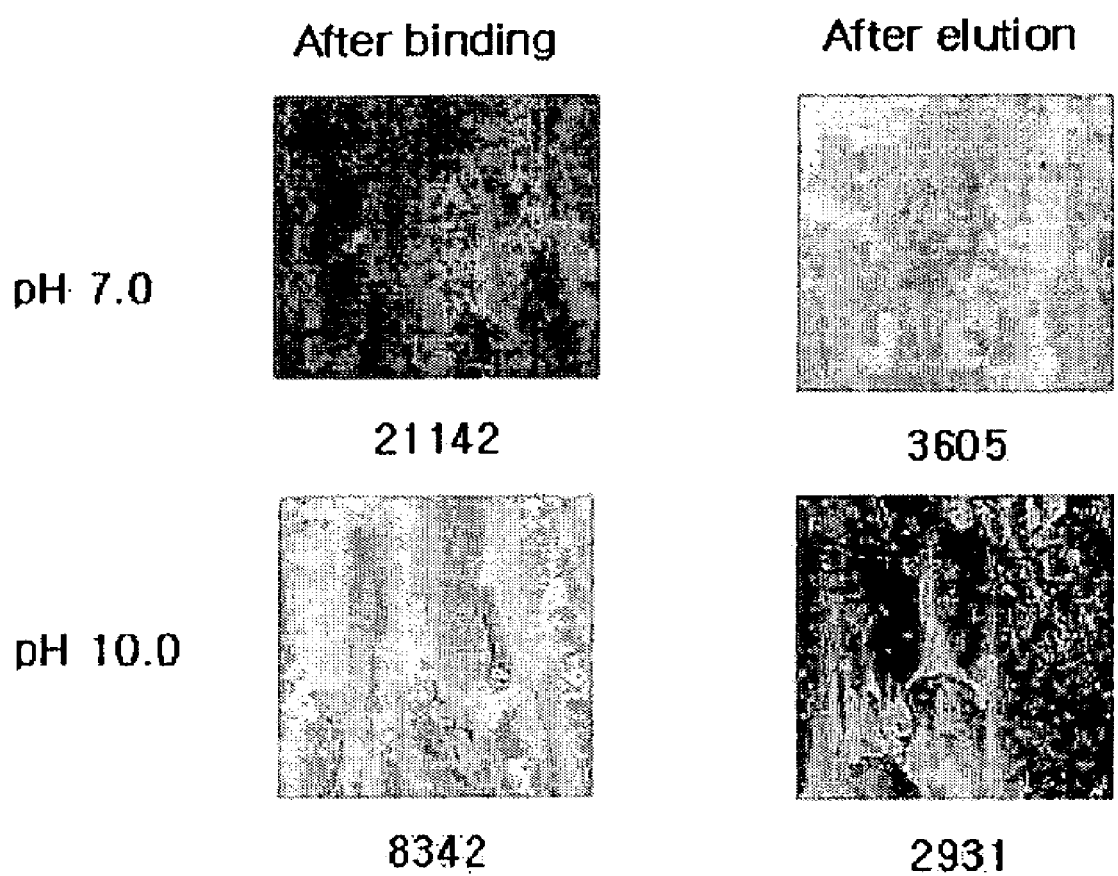
FIG. 6 is fluorescence intensities, as measured by a laser scanner, of Cy3-labelled 50-mer oligonucleotides bound to and eluted from a PEG-hydrogel copolymer.

To evaluate whether DNAs can be isolated and purified by a PEG-hydrogel copolymer immobilized on a substrate, a PEG-hydrogel copolymer was synthesized in the same manner as in Synthesis Example 2 using poly(ethylene-alt-maleic anhydride) having an average molecular weight of 300,000 except that the ratio of PEG to maleic acid was 2.5%. 1 M (final) of NaCl and 10 nM (final) of Cy3-labelled 50-mer oligonucleotides were added to the synthesized PEG-hydrogel copolymer and incubated at room temperature for 5 minutes. 0.1 M of phosphate (pH 7.0) and 0.1 M sodium carbonate (pH 10.0) were used as binding buffers. Then, the oligonucleotide-bound hydrogel was once washed with 60 µl of 70% EtOH for 5 minutes, and the oligonucleotides were eluted with 60 µl of distilled water for 10 minutes. FIG. 6 is fluorescence intensities, as measured by a laser scanner, of the Cy3-labelled 50-mer oligonucleotides bound to and eluted from the PEG-hydrogel copolymer. Higher fluorescence intensity indicates the binding of more oligonucleotides to the PEG-hydrogel copolymer. Referring to FIG. 6, it can be seen that DNAs can be bound to and eluted from a PEG-hydrogel copolymer-immobilized substrate. Furthermore, DNA binding more easily occurred at pH 7.0 relative to at pH 10.0 by about 2.5 times. Therefore, it can be seen that the use of a method of the present invention enables efficient isolation and purification of nucleic acids from a nucleic acid-containing sample.

Example 4

Separation Efficiency of DNAS by Peg-hydrogel Copolymer According to PEG Ratio

Figure 7:
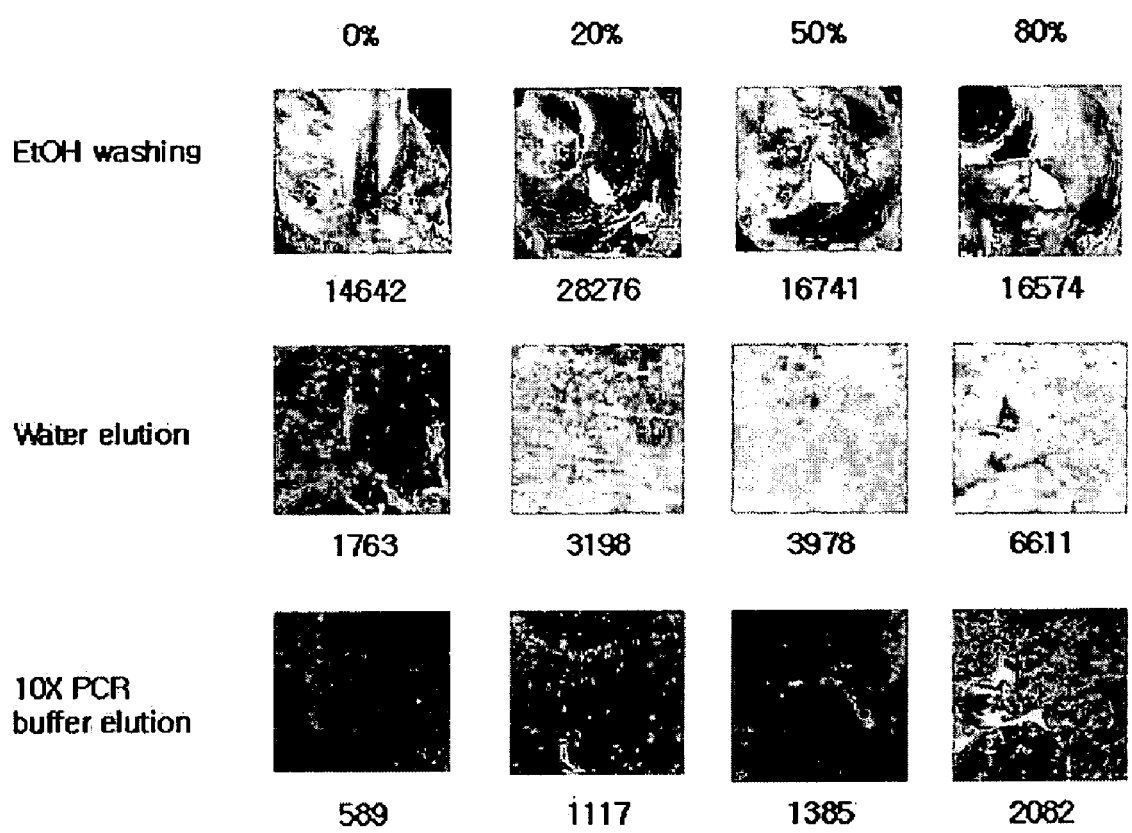
FIG. 7 is fluorescence intensities, as measured by a laser scanner, of Cy3-labelled 50-mer oligonucleotides bound to PEG-hydrogel copolymers with different PEG ratios after washing with 70% EtOH, elution with water, and elution with a 10× PCR buffer.
Figure 8:
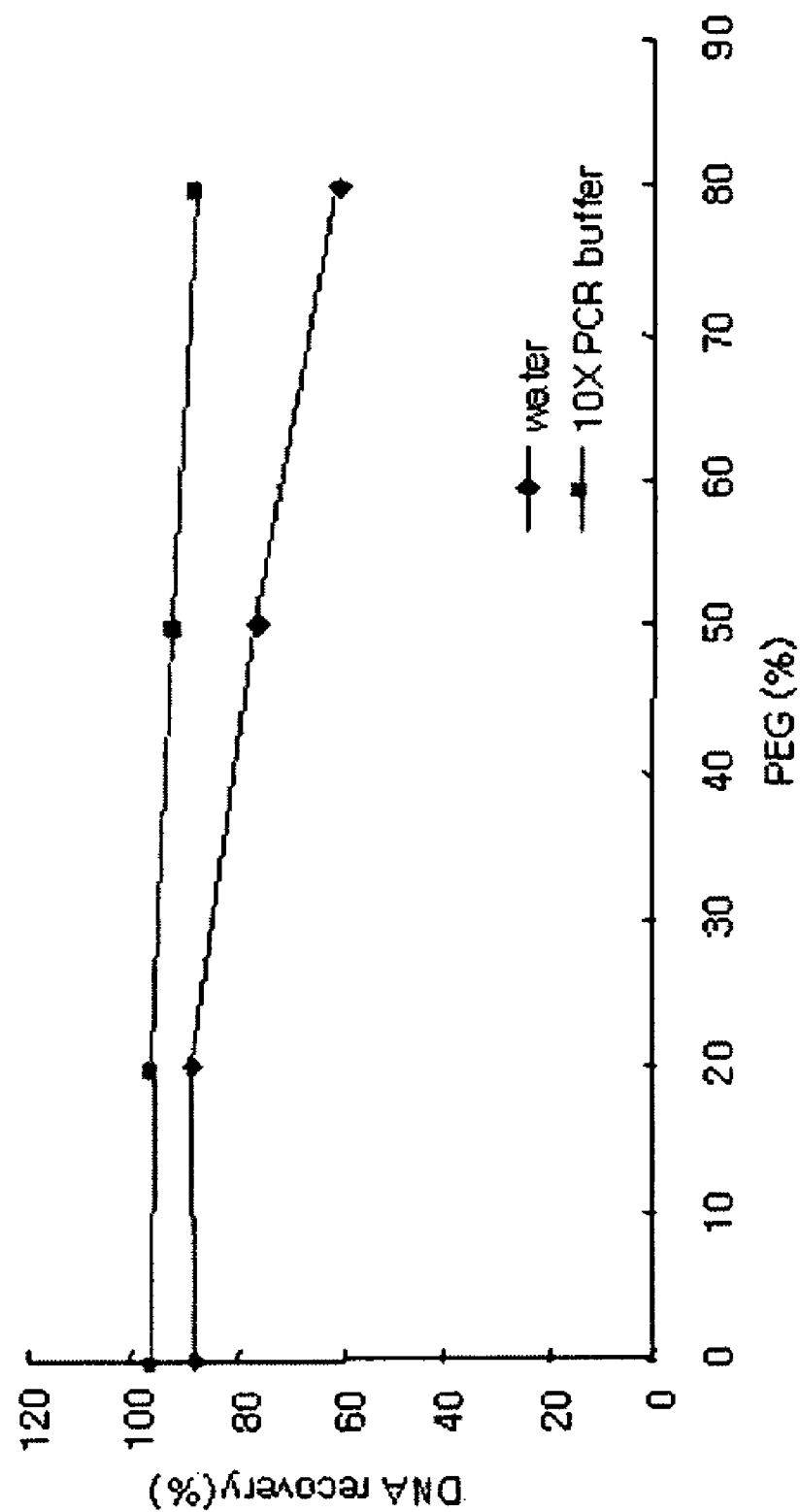
FIG. 8 is a graph illustrating a DNA recovery with respect to water and a 10× PCR buffer used as an elution solvent.

To evaluate the separation efficiency of DNAs by a PEG-hydrogel copolymer according to a PEG incorporation ratio, four PEG-hydrogel copolymers were synthesized in the same manner as in Synthesis Example 2 except that poly(ethylene-alt-maleic anhydride) having an average molecular weight of 150,000 was used, and the ratio of PEG to maleic acid group was 0%, 20%, 50%, and 80%, respectively. The separation efficiency of DNAs by the PEG-hydrogel copolymers was evaluated in the same manner as in Example 3 except that 0.1 M phosphate (pH 7.0) was used as a binding buffer. FIG. 7 is fluorescence intensities, as measured by a laser scanner, of Cy3-labelled 50-mer oligonucleotides bound to the PEG-hydrogel copolymers with different PEG ratios, after washing with 70% EtOH, elution with water, and elution with a 10× PCR buffer. Higher fluorescence intensity indicates the binding of more oligonucleotides to a PEG-hydrogel copolymer. As shown in FIG. 7, the largest number of the oligonucleotides was bound to the PEG-hydrogel copolymer with the PEG incorporation ratio of 20%. After the elution with an elution solvent such as water or 10× PCR buffer (750 mM Tris-HCl, 150 mM $(NH_4)_2SO_4$, 10 µg/ml BSA, 25 mM $MgCl_2$), fluorescence intensity was remarkably reduced, which shows that most oligonucleotides were eluted by the elution solvent. FIG. 8 is a graph illustrating a DNA recovery with respect to water and a 10× PCR buffer used as an elution solvent. As shown in FIG. 8, the DNA recovery was the highest when the PEG incorporation ratio was 20% and decreased with increase in the PEG incorporation ratio. Furthermore, the DNA recovery using a 10× PCR buffer was better than that using water.

Example 5

PCR Amplification Efficiency of Eluted DNAs

DNA separation was performed in the same manner as in Example 4 except that hepatitis B virus (HBV) plasmid DNAs (7 kb) were used instead of Cy3-labelled 50-mer oligonucleotides. Real-time PCR for the DNAs thus separated was performed. The PCR amplification was performed in 20 µl volume using a LightCycler machine (Roche Diagnostics, Mannheim, Germany). The core region of the HBV genome was amplified using a forward primer (SEQ ID NO: 1) and a reverse primer (SEQ ID NO: 2). A mastermix for the LightCycler reaction was prepared using the following components: 2 µl LightCycler master (Fast start DNA master SYBR Green I; Roche Diagnostics), 3.2 µl $MgCl_2$ (5 mM), 1.0 µl forward-reverse primer mixture (1.0 µM), 4.0 µl UNG (Uracil-N-Glycosylase, 0.2 unit), and 4.8 µl $H_2O$. A 5 µl of an analyte was added to the mastermix. Two types of Taq DNA polymerases, i.e., Roche Hot-start Taq DNA polymerase and Solgent Taq DNA polymerase, were used in preparation of the LightCycler master.

PCR using the Roche Hot-start Taq DNA polymerase was performed as follows: pre-denaturation at 50° C. for 10 minutes and at 95° C. for 10 minutes and then 35 cycles (denaturation at 95° C. for 5 seconds, annealing and extension at 62° C. for 15 seconds). On the other hand, PCR using the Solgent Taq DNA polymerase was performed as follows: pre-denaturation at 50° C. for 10 minutes and at 95° C. for one minute and then 35 cycles (denaturation at 95° C. for 5 seconds, annealing and extension at 62° C. for 15 seconds).

The amplified DNAs were analyzed in an Agilent 2100 BioAnalyzer (Agilent Technologies, Palo Alto, Calif.) using commercially available DNA 500 assay sizing reagent sets.

Figure 9:
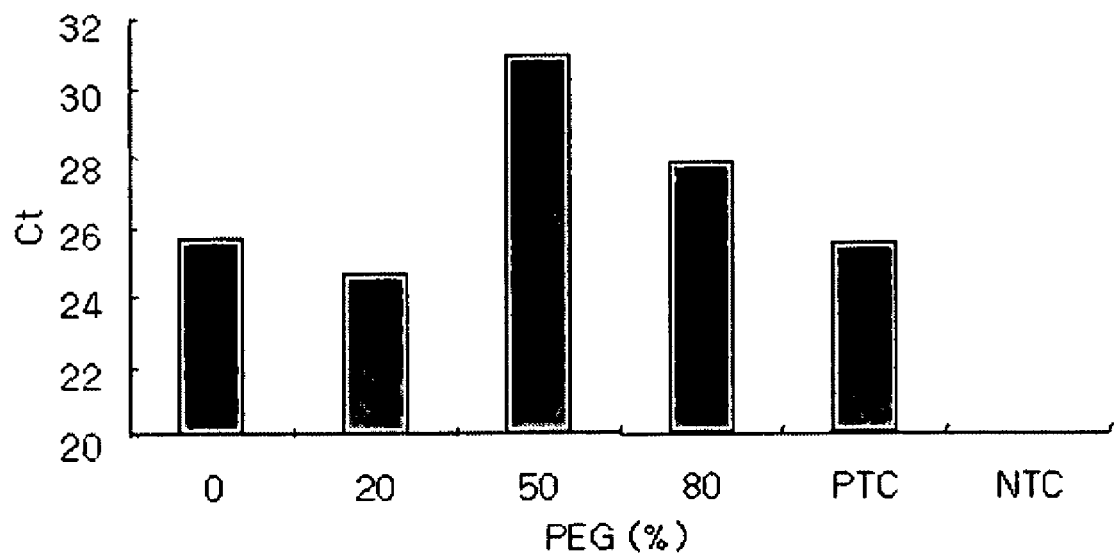
FIG. 9 is a count of threshold (Ct) graph for the results of PCR using, as templates, DNAs separated from immobilized PEG-hydrogel copolymers with different PEG ratios.

FIG. 9 is a count of threshold (Ct) graph for the results of PCR using, as templates, DNAs separated from immobilized PEG-hydrogel copolymers with different PEG ratios. In FIG. 9, PTC is a positive control showing PCR result using HBV plasmid DNAs and NTC is a negative control showing PCR result using distilled water. The PCR results were represented by Ct values. Ct indicates the number of cycles for which an initial fluorescence signal is observed in real-time PCR. In PCR, as the number of initial template DNA molecules is larger, a smaller Ct value is obtained. On the other hand, as the number of initial template DNA molecules is smaller, a larger Ct value is obtained. As shown in FIG. 9, PCR was performed for all the four types of PEG incorporation ratios. The lowest Ct value was obtained at the PEG incorporation ratio of 20%, which shows that the largest amount of DNAs were isolated at the PEG incorporation ratio of 20%. This result was consistent with the DNA recovery result of Example 4 using the Cy3-labelled 50-mer oligonucleotices in which the highest DNA recovery was obtained at the PEG incorporation ratio of 20%.

Figure 10:
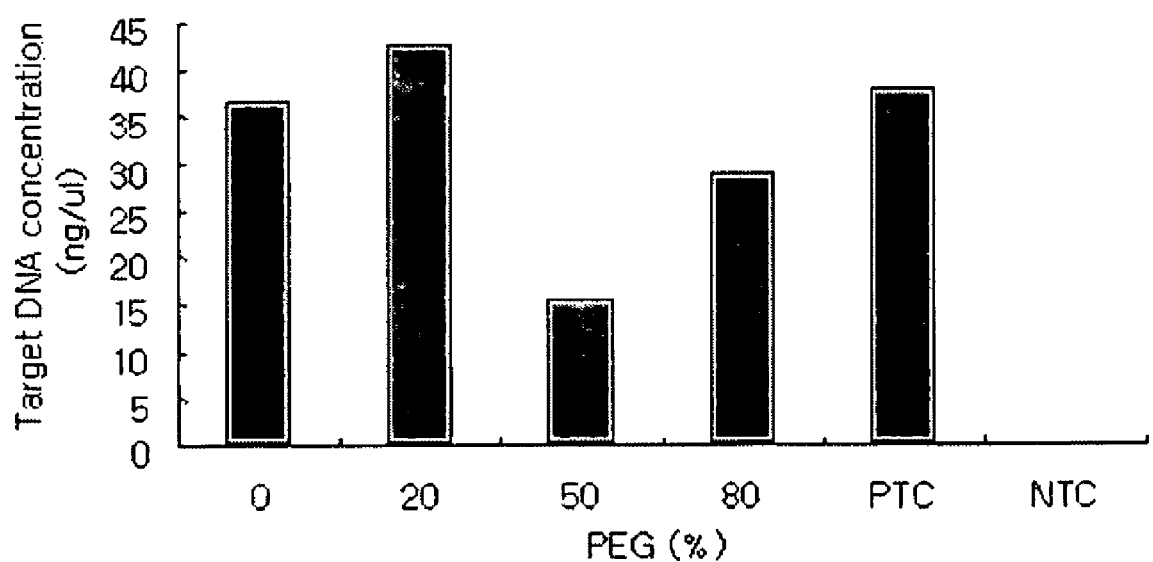
FIG. 10 illustrates an amplified DNA concentration by PCR using, as templates, DNAs separated by immobilized PEG-hydrogel copolymers with different PEG ratios.

To determine whether the Ct value is directly related with production of target PCR products, that is, whether the reduction of the Ct value is caused by production of more target PCR products, the concentration of target PCR products was measured. FIG. 10 illustrates the concentration of amplified DNAs by PCR using, as templates, DNAs separated by immobilized PEG-hydrogel copolymers with different PEG ratios. In FIG. 10, PTC is a positive control showing PCR result using HBV plasmid DNAs and NTC is a negative control showing PCR result using distilled water. The concentration (ng/μl) of the amplified DNAs was represented by histogram. PCR products were quantified by Agilent 2100 BioAnalyzer. As shown in FIG. 10, PCR products were obtained at all the four types of PEG incorporation ratios. The largest amount of the PCR products was obtained at the PEG incorporation ratio of 20%.

Example 6

Effect of Hydrogel on DNA Binding

Figure 11:
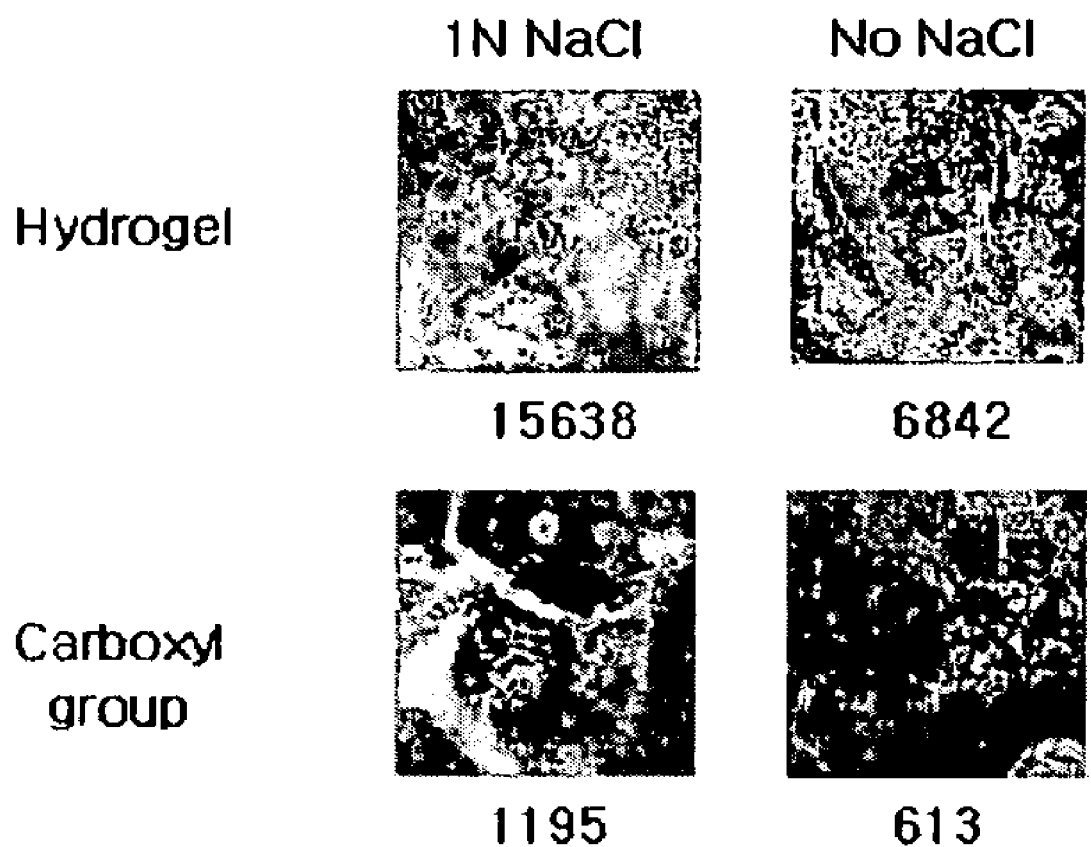
FIG. 11 is fluorescence intensities, as measured by a laser scanner, of Cy3-labelled 50-mer oligonucleotides bound to two substrates containing carboxyl group in the presence or absence of 1M NaCl.

To evaluate the effect of hydrogel on DNA binding, a hydrogel-immobilized substrate and a carboxyl group-immobilized substrate were prepared. This Example was performed in the same manner as Example 3 except that elution was omitted. FIG. 11 is fluorescence intensities, as measured by a laser scanner, of Cy3-labelled 50-mer oligonucleotides bound to the two substrates containing carboxyl group in the presence or absence of 1 M NaCl. As shown in FIG. 11, the binding of the hydrogel with the oligonucleotides was good at high salt concentration. On the other hand, the binding of the oligonucleotides with the carboxyl group-immobilized substrate scarcely occurred regardless of salt concentration. From these results, it can be seen that a major material binding with DNAs is hydrogel and PEG serves to increase an amount and an intensity for binding DNAs.

Therefore, it can be seen that DNAs can be efficiently isolated and purified using a hydrogel or PEG-hydrogel copolymer immobilized on a substrate.

As apparent from the above description, according to the present invention, nucleic acids can be isolated and purified using a hydrogel or a PEG-hydrogel copolymer immobilized on a substrate. Therefore, binding and elution of nucleic acids can be performed even with no addition of a separate chemical substance, and an effect on a subsequent process such as PCR can be minimized. Furthermore, the amount and intensity for binding nucleic acids can be adjusted according to PEG concentration, and the presence of a hydrogel compound on a substrate enables patterning.

What is claimed is:

1. A method of isolating and purifying nucleic acids using an immobilized polyethylene glycol (PEG)-containing hydrogel, the method comprising:
   immobilizing a polyethylene glycol (PEG)-containing hydrogel on a substrate;
   adding a mixed sample solution containing a salt and nucleic acids to the PEG-containing hydrogel immobilized substrate to bind the nucleic acids to the PEG-containing hydrogel;
   washing the nucleic acid-bound PEG-containing hydrogel;
   eluting the nucleic acids from the nucleic acid-bound PEG-containing hydrogel using an elution solvent, and recovering the eluted nucleic acids,
   wherein the PEG-containing hydrogel is a reaction product of PEG and a polymer represented by formula I below,
   wherein an incorporation ratio of the PEG is 1 to 20 mole % based on carboxyl groups formed from hydrolysis of the polymer of formula I and the PEG is bound to the carboxyl groups of the hydrolyzed polymer via an ester bond:

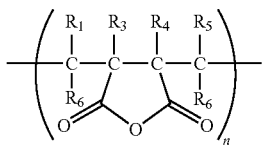

(I)

wherein,
$R_1$ through $R_6$ are each independently a hydrogen atom, a halogen atom, a hydroxy group, a substituted or unsubstituted alkyl group of 1-20 carbon atoms, a substituted or unsubstituted alkoxy group of 1-20 carbon atoms, a substituted or unsubstituted alkenyl group of 1-20 carbon atoms, a substituted or unsubstituted aryl group of 6-30 carbon atoms, a substituted or unsubstituted aryloxy group of 6-30 carbon atoms, a substituted or unsubstituted heteroaryl group of 2-30 carbon atoms, or a substituted or unsubstituted heteroaryloxy group of 2-30 carbon atoms;
and n is an integer from 2 to 100,000.

2. The method of claim 1, wherein the substrate is a water-insoluble solid selected from the group consisting of a slide glass, a silicon wafer, a metal plate, and a polystyrene film.

3. The method of claim 1, wherein the salt is a halogen salt of an alkali metal or an alkali earth metal, and the concentration of the salt is in the range from 0.5 to 5 M.

4. The method of claim 3, wherein the salt is selected from the group consisting of sodium chloride, lithium chloride, potassium chloride, calcium chloride, barium chloride, magnesium chloride, and cesium chloride.

5. The method of claim 1, wherein the nucleic acids are selected from the group consisting of DNAs, RNAs, PNAs, and LNAs.

6. The method of claim 1, wherein the elution solvent is water.

7. The method of claim 1, wherein a molecular weight of the PEG is in the range from 2,000 to 10,000 Daltons.

8. The method of claim 1, wherein the polyethylene glycol (PEG)-containing hydrogel is covalently immobilized to the substrate.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: artificial
<220> FEATURE:
<223> OTHER INFORMATION: forward primer

<400> SEQUENCE: 1
agtgtggatt cggcactcct                     20

<210> SEQ ID NO 2
<211> LENGTH: 23
<212> TYPE: DNA
<213> ORGANISM: artificial
<220> FEATURE:
<223> OTHER INFORMATION: reverse primer

<400> SEQUENCE: 2
gagttcttct tctaggggac ctg                 23